(12) United States Patent
Nimura et al.

(10) Patent No.: US 10,124,106 B2
(45) Date of Patent: Nov. 13, 2018

(54) BLOOD PURIFICATION APPARATUS

(71) Applicant: Nikkiso Company Limited, Tokyo (JP)

(72) Inventors: Hiroshi Nimura, Makinohara (JP);
Kazumi Yokoyama, Makinohara (JP);
Tomohiro Furuhashi, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 232 days.

(21) Appl. No.: 14/191,915

(22) Filed: Feb. 27, 2014

(65) Prior Publication Data
US 2014/0174997 A1 Jun. 26, 2014

Related U.S. Application Data

(63) Continuation of application No. PCT/JP2012/072210, filed on Aug. 31, 2012.

(30) Foreign Application Priority Data

Aug. 31, 2011 (JP) ................. 2011-189282

(51) Int. Cl.
| | | |
|---|---|---|
| *A61M 1/30* | (2006.01) | |
| *A61M 1/16* | (2006.01) | |
| *A61M 1/36* | (2006.01) | |
| *A61M 1/34* | (2006.01) | |

(52) U.S. Cl.
CPC .............. *A61M 1/306* (2014.02); *A61M 1/16* (2013.01); *A61M 1/3465* (2014.02); *A61M 1/365* (2014.02); *A61M 1/3621* (2013.01); *A61M 1/3627* (2013.01); *A61M 1/3646* (2014.02); *A61M 1/3649* (2014.02)

(58) Field of Classification Search
CPC ...... A61M 1/16; A61M 1/306; A61M 1/3465; A61M 1/3621; A61M 1/3627; A61M 1/3646; A61M 1/3649; A61M 1/365
USPC ........................................... 210/137
See application file for complete search history.

(56) References Cited

U.S. PATENT DOCUMENTS

| | | |
|---|---|---|
| 5,529,685 A | 6/1996 | Irie et al. |
| 2005/0230314 A1 | 10/2005 | Kim et al. |
| 2006/0079826 A1 | 4/2006 | Beden et al. |
| 2010/0274172 A1 | 10/2010 | Guenther et al. |

FOREIGN PATENT DOCUMENTS

| | | |
|---|---|---|
| JP | 06-261938 | 9/1994 |
| JP | 2003-180823 | 7/2003 |
| JP | 2004-313522 | 11/2004 |
| JP | 2006-280775 | 10/2006 |
| JP | 2011-160924 | 8/2011 |
| JP | 2012-152285 | 8/2012 |

*Primary Examiner* — Dirk R Bass
(74) *Attorney, Agent, or Firm* — Harness, Dickey & Pierce, P.L.C.

(57) ABSTRACT

The blood purification apparatus has a control device (19) that performs a venous returning blood process S1, an arterial returning blood process S4 and a negative pressure applying process S1a. The returning of the blood is performed by substituting a physiological saline solution for the blood in the blood circuit. The negative pressure applying process S1a releases a negative pressure after applying the negative pressure to a flow route on an upstream side from an arrangement position of a blood pump 4 in the arterial blood circuit (1). The blood pump (4) is in a normal rotation and an electromagnetic valve V3 switches over the physiological saline solution supplying line 8 from a closing state to a circulating state.

10 Claims, 10 Drawing Sheets

[Fig 1]
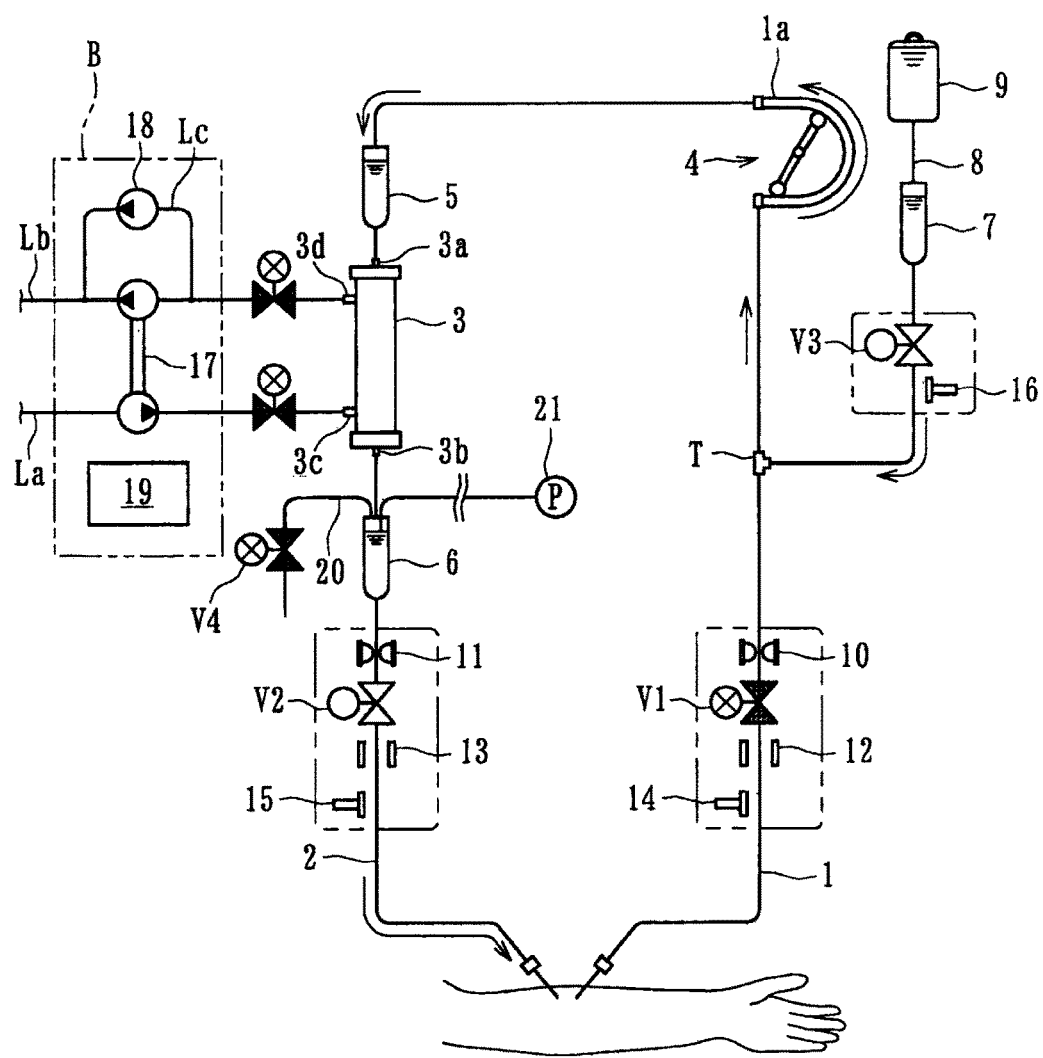

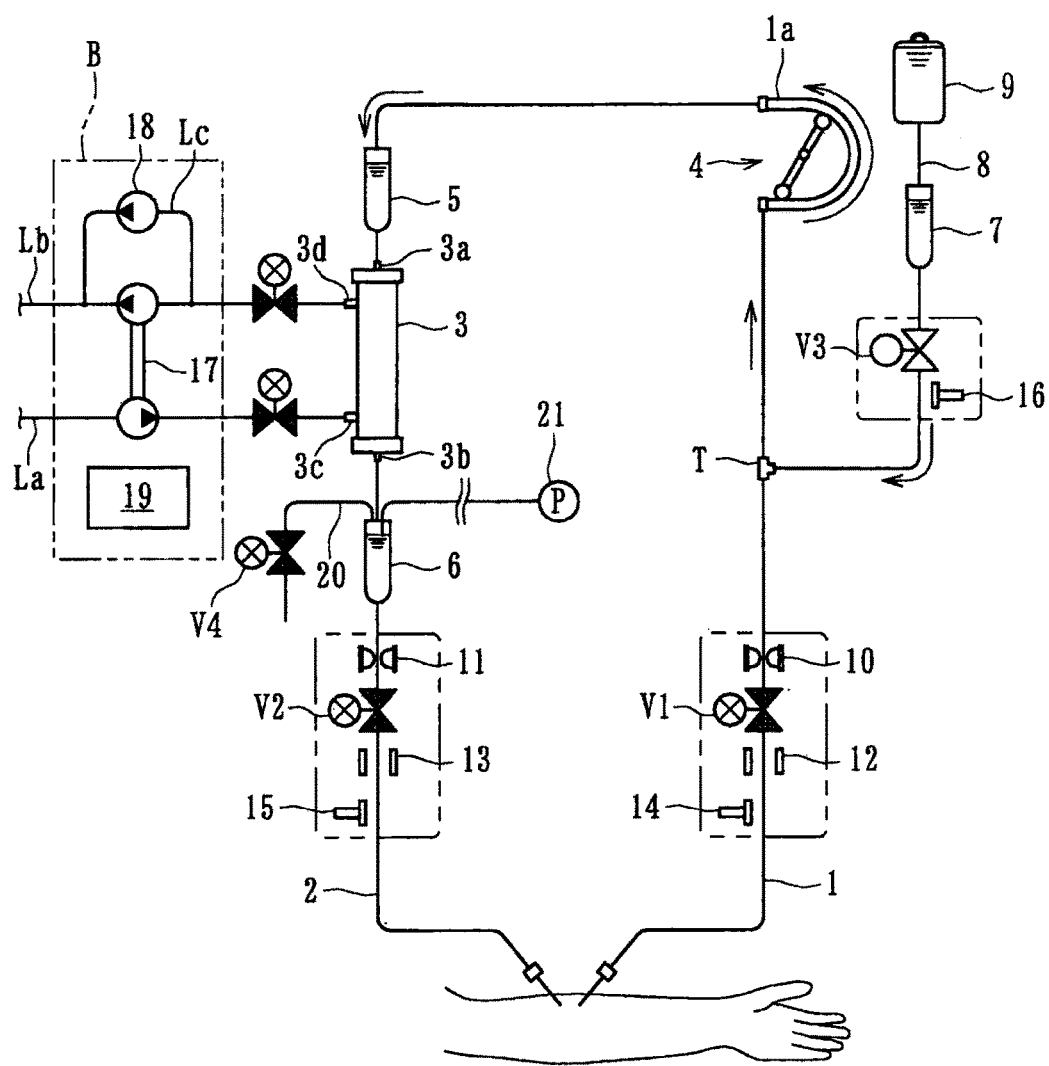
[Fig 2]

[Fig 3]
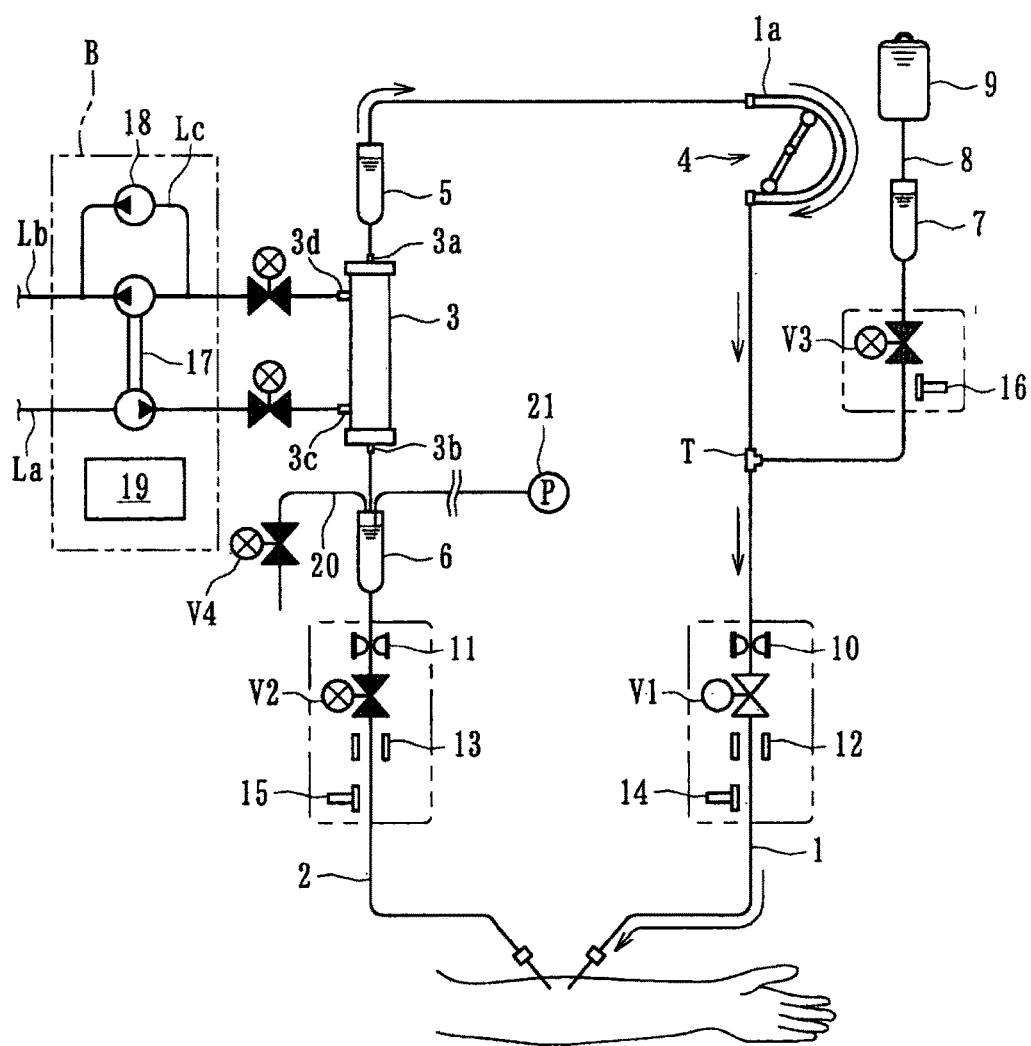

[Fig 4]
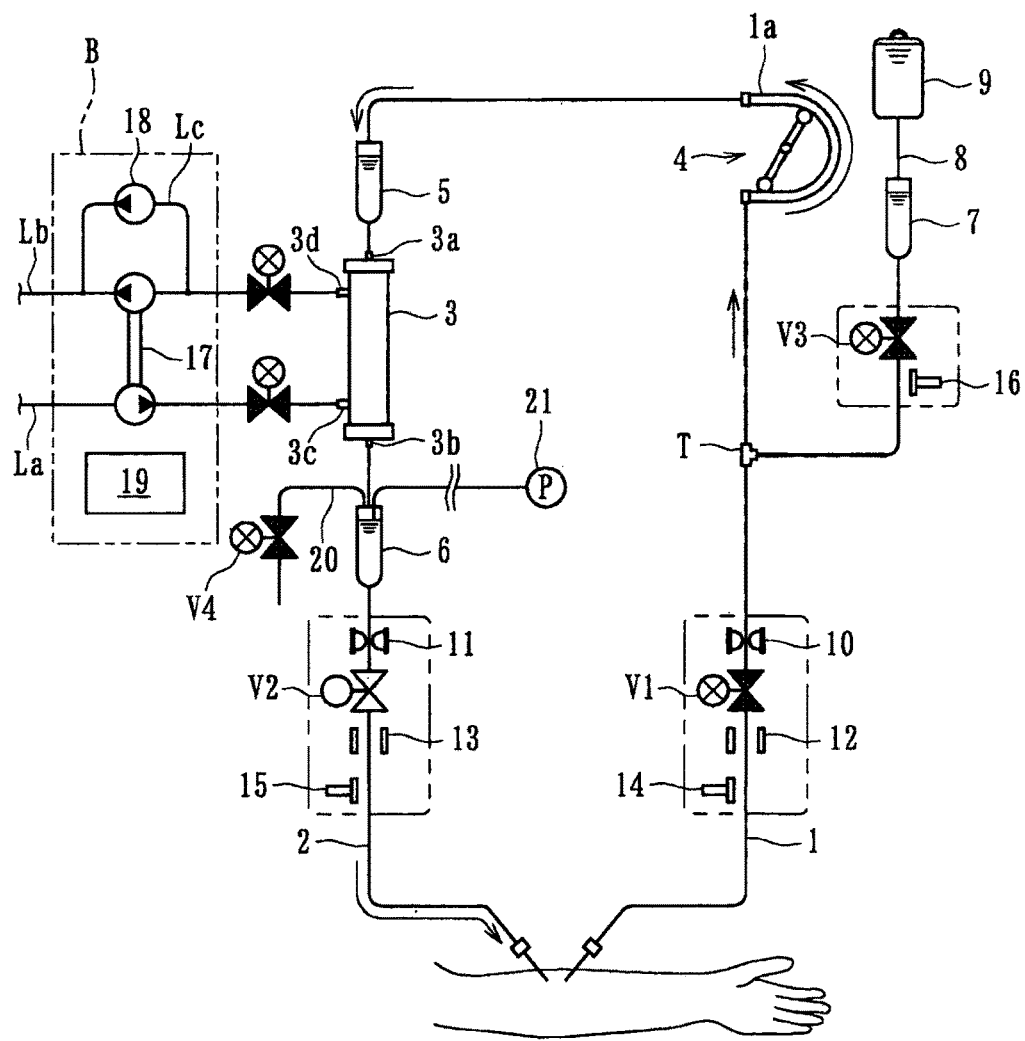

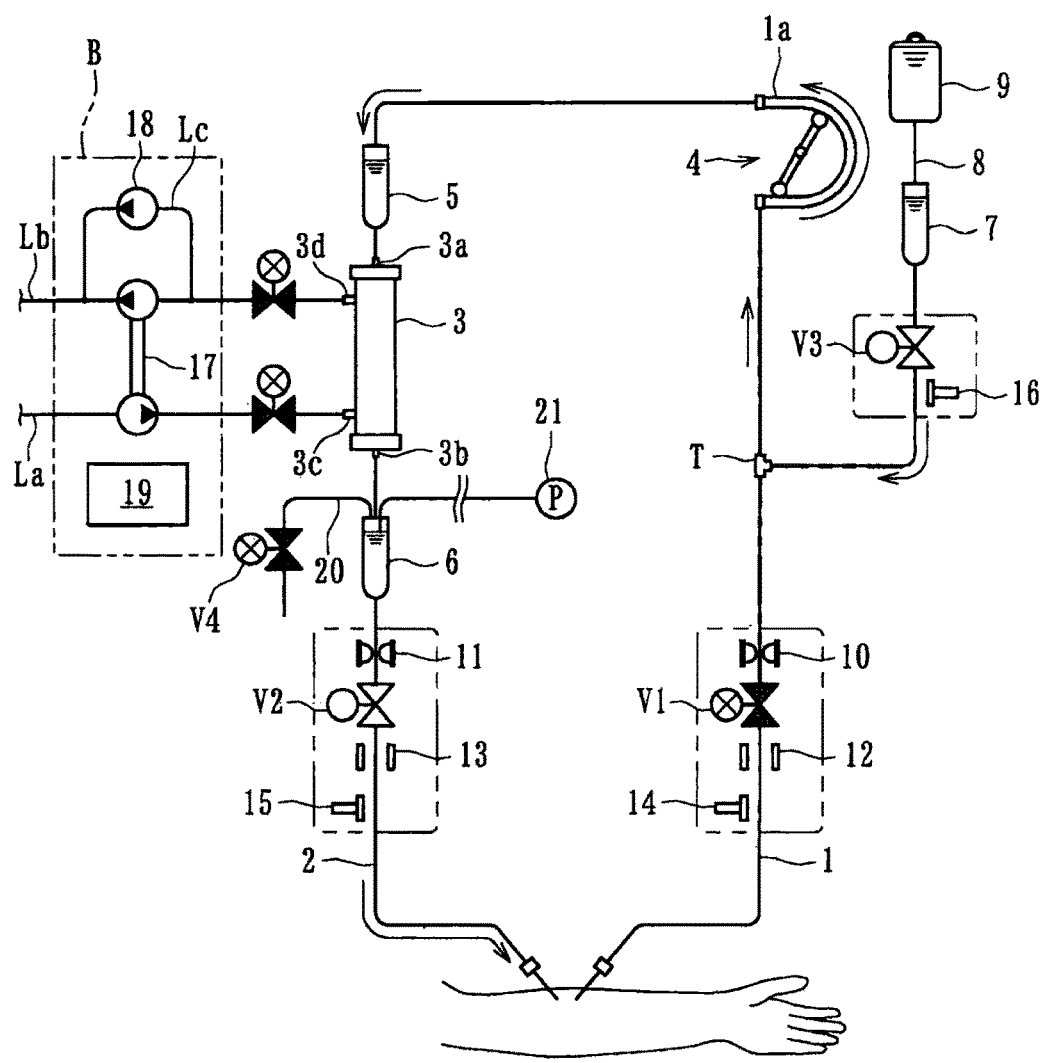
[Fig 5]

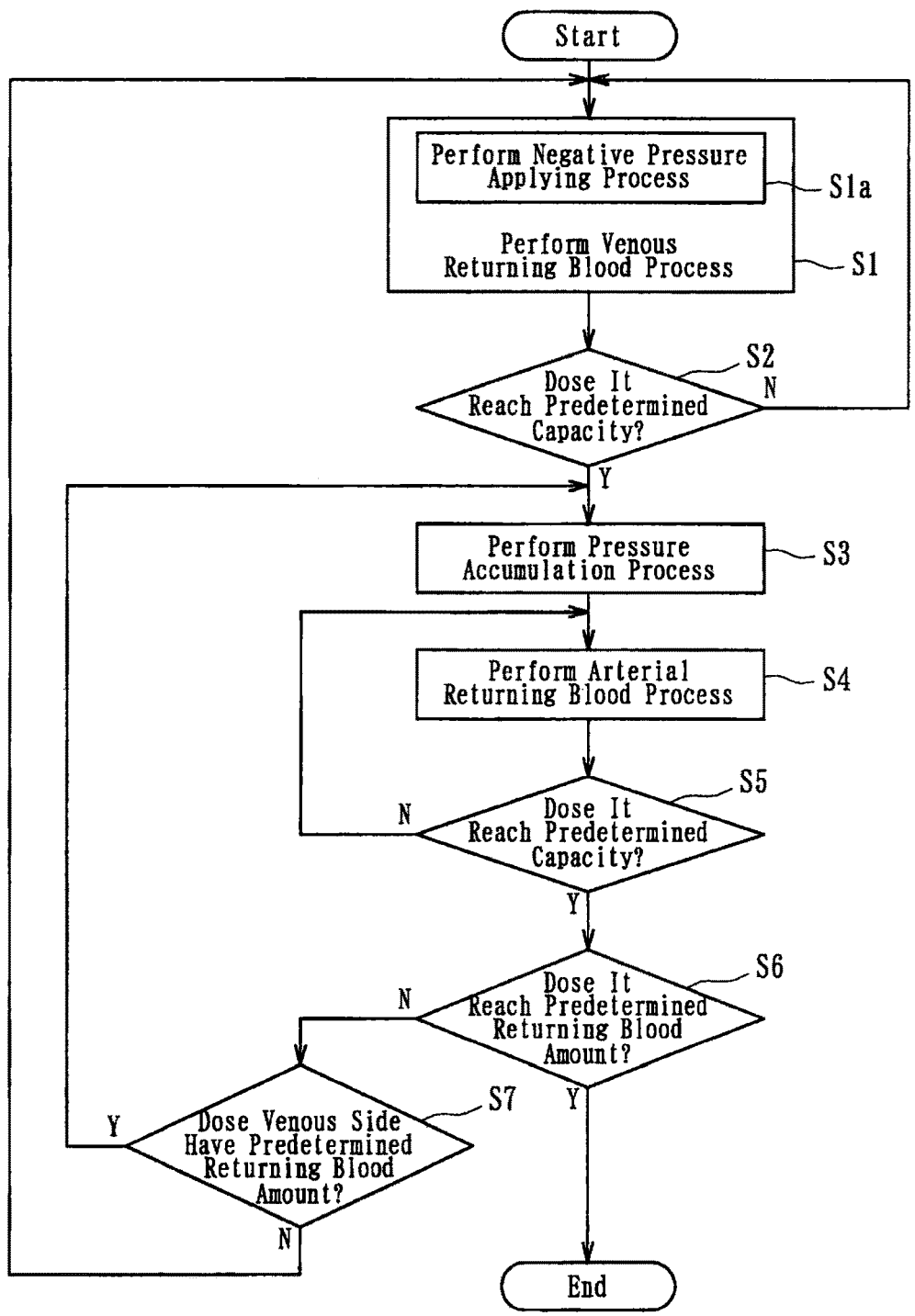
[Fig 6]

[Fig 7]
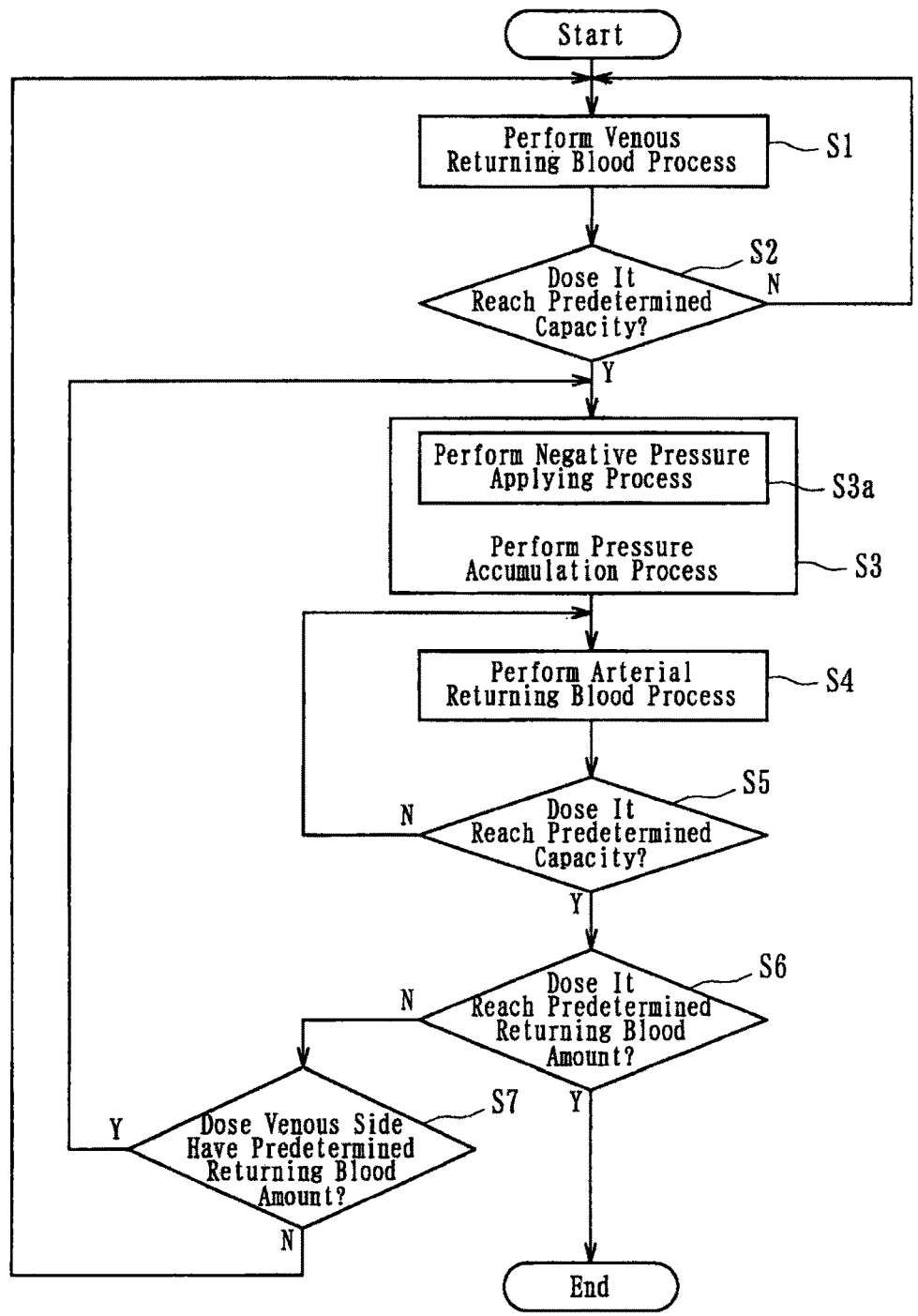

[Fig 8]
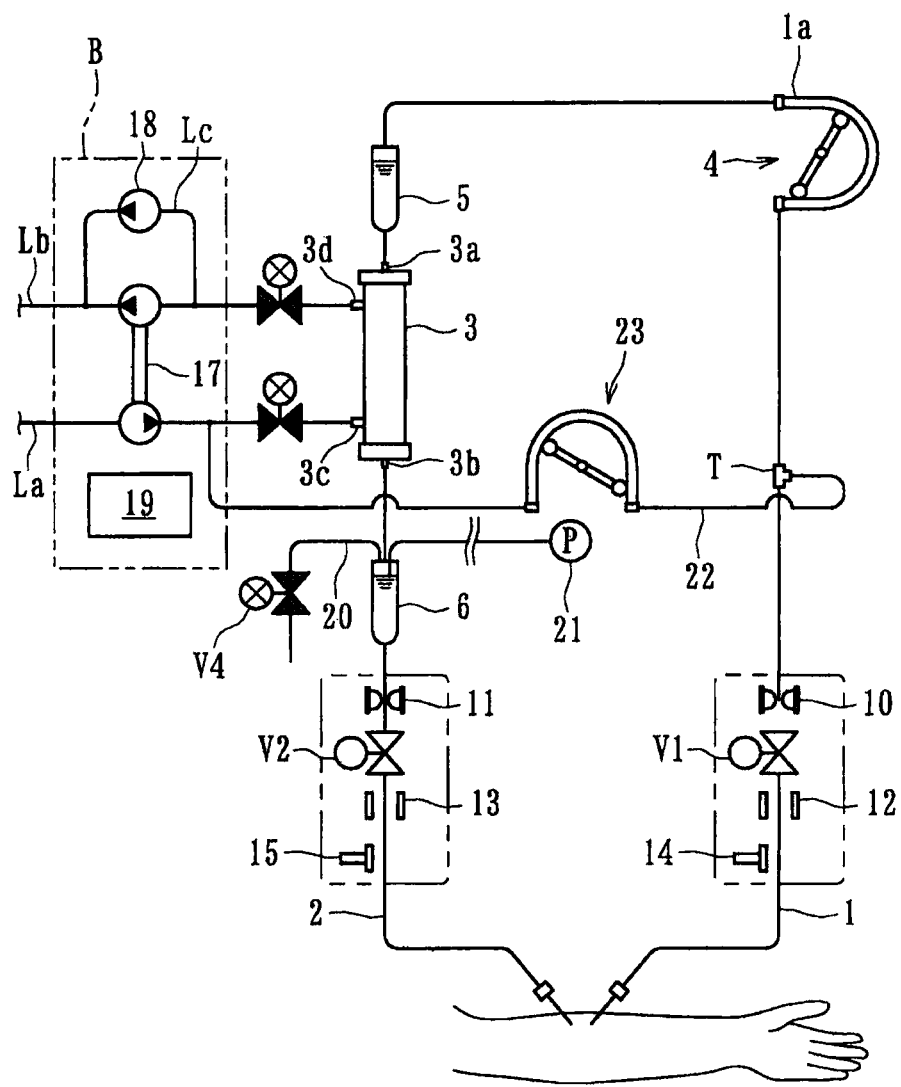

[Fig 9]
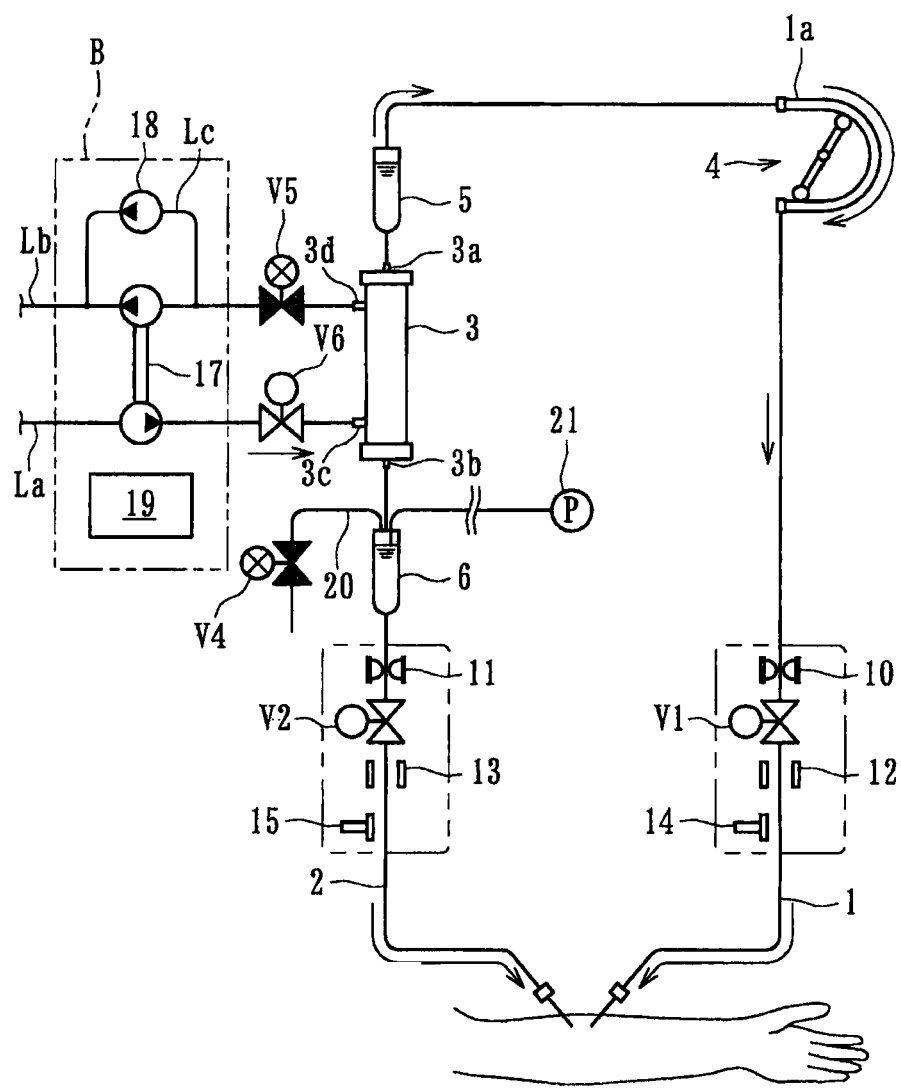

[Fig 10]
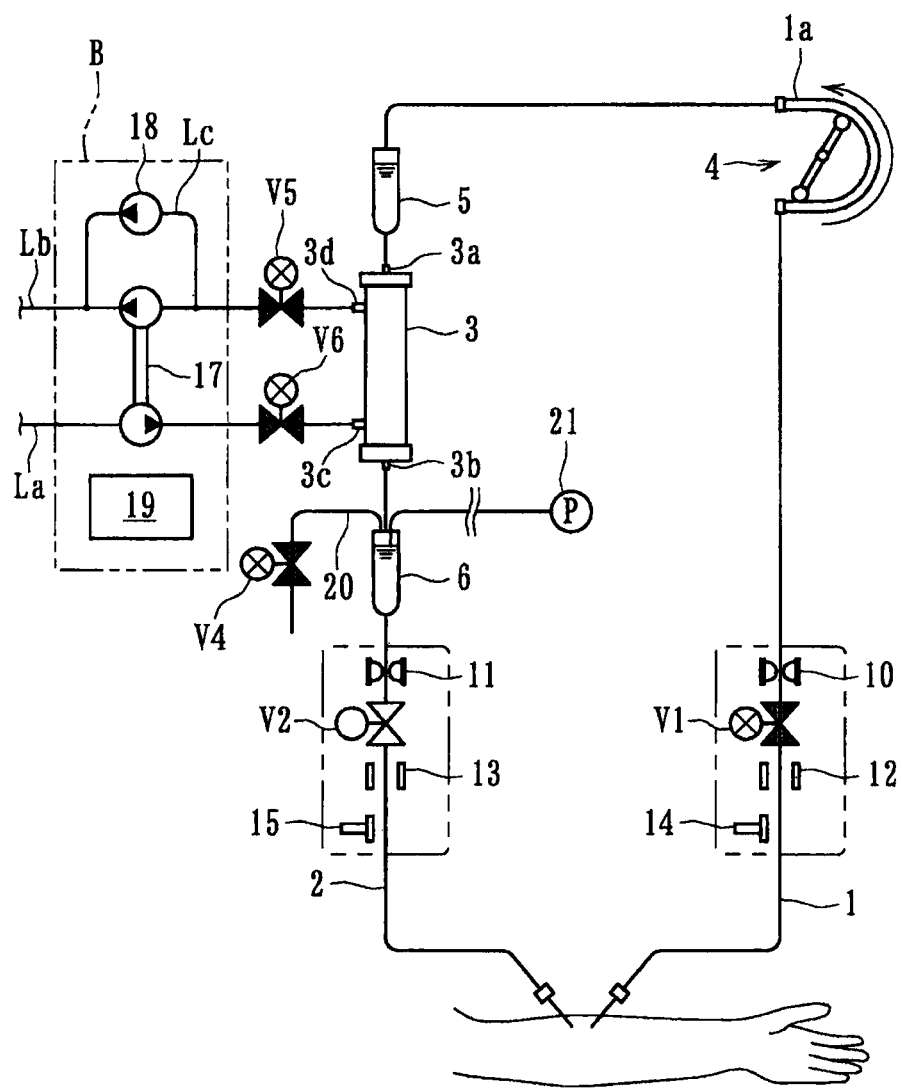

BLOOD PURIFICATION APPARATUS

CROSS-REFERENCE TO RELATED APPLICATIONS

This application is a continuation of International Application No. PCT/JP2012/072210, filed Aug. 31, 2012, which claims priority to Japanese Application No. 2011-189282, filed Aug. 31, 2011. The disclosures of the above applications are incorporating herein by reference.

FIELD

The present disclosure relates to a blood purification apparatus that extracorporeally circulates blood of a patient to purify the blood in a dialyzer used for dialysis treatment.

BACKGROUND

A dialysis apparatus as a blood purification apparatus is mainly configured to include a blood circuit with an arterial blood circuit and a venous blood circuit. The arterial blood circuit has an arterial puncture needle attached to its distal end. The venous blood circuit includes a venous puncture needle attached to its distal end. A dialyzer is interposed between the arterial blood circuit and the venous blood circuit. The dialyzer purifies blood flowing in the blood circuit. A blood pump is arranged in the arterial blood circuit. An arterial air trap chamber and a venous air trap chamber are, respectively, arranged in the arterial blood circuit and the venous blood circuit. The air trap chambers remove air bubbles. A dialysis device supplies a dialysate to the dialyzer.

In addition, a containing bag contains a physiological saline solution. The containing bag is connected, via a physiological saline solution supplying line, between the arterial puncture needle and the blood pump in the arterial blood circuit. When priming before dialysis treatment, the physiological saline solution inside the containing bag can be supplied into the blood circuit via the physiological saline solution supplying line. Thus, substitution during the dialysis treatment or returning of blood after the dialysis treatment is performed. For example, during the returning of blood, the returning of blood can be performed by supplying the physiological saline solution into the blood circuit as a substitution solution. This substitutes the blood inside the blood circuit with the substitution solution (for example, refer to Japanese Unexamined Patent Application Publication No. 2006-280775).

Incidentally, in recent years, in order to reduce the burden on health care workers, there has been an increased need to automate various procedures during blood purification treatment. For example, a blood purification apparatus has been proposed that includes a control device to alternately control a returning blood process. During returning of the blood, the returning of the blood is performed by allowing the blood pump to be in a normal rotation and substituting the substitution solution for the blood. A connection portion connects a substitution solution supplying line to a distal end of the venous blood circuit in the blood circuit. This is referred to as a venous returning blood process. The returning of blood is performed by allowing the blood pump to be in a reverse rotation and substituting the substitution solution for the blood. The connection portion connects the substitution solution supplying line to a distal end of the arterial blood circuit in the blood circuit. This is referred to as an arterial returning blood process (for example, refer to Japanese Unexamined Patent Application Publication No. 6-261938).

SUMMARY

However, the above-described blood purification apparatus in the related art has the following problems.

While the blood is extracorporeally circulated during the blood purification treatment, air bubbles are likely to be accumulated in an upstream side. This is from an arrangement position of the blood pump in the arterial blood circuit or a connection portion connected to the physiological saline solution supplying line (T-tube and the like). Specifically, an upstream portion of a peristaltically-actuated tube that is connected to the arterial blood circuit and is peristaltically actuated by the blood pump. In particular, the upstream side from the arrangement position of the blood pump in the arterial blood circuit is likely to have a relative negative pressure. Oxygen dissolved in the blood is likely to become air bubbles.

However, in general, the venous air trap chamber, for removing air bubbles, is connected to the venous blood circuit. Accordingly, during a venous returning blood process, where the returning of blood is performed by allowing the blood pump to be in the normal rotation, and substituting of the substitution solution for the blood, the connection portion connects the substitution solution supplying line to the distal end of the venous blood circuit in the blood circuit. Thus, the venous air trap chamber can capture air bubbles accumulated in the treatment.

In contrast, in general, the air trap chamber, for removing air bubbles, is not connected to a section from the arrangement position of the blood pump to the distal end of the arterial blood circuit in the arterial blood circuit. Accordingly, during an arterial returning blood process, where the returning of blood is performed by allowing the blood pump to be in the reverse rotation and substituting the substitution solution for the blood, the connection portion connects the substitution solution supplying line to the distal end of the arterial blood circuit in the blood circuit. Air bubbles accumulated in the treatment are caused to flow to the distal end side of the arterial blood circuit. Then, an air bubble detection device, arranged in the distal end portion of the arterial blood circuit, detects air bubbles and issues an alarm.

If the alarm is issued, it is necessary for the health care workers to immediately go to the blood purification apparatus and perform an operation for stopping the alarm. Thus, effort is required, causing a problem in the automation effects. In addition, while an alarm is issued, the returning of the blood operation is generally stopped. Accordingly, the blood flow inside the blood circuit is stopped. This causes a problem with an increased risk of coagulated blood. Without being limited to a case where the venous returning blood process and the arterial returning blood process are performed during the returning of blood, these problems similarly occur in a case where a dialysate is used as the substitution solution by means of back-filtration of the dialysate from the dialyzer to the blood circuit side.

The present disclosure is made in view of the above-described circumstances. The disclosure aims to provide a blood purification apparatus that can suppress air bubbles from flowing into a distal end of an arterial blood circuit. Thus, this can reduce the burden on health care workers.

According to the disclosure, a blood purification apparatus includes a blood circuit with an arterial blood circuit and a venous blood circuit that extracorporeally circulates patient's blood from a distal end of the arterial blood circuit to a distal end of the venous blood circuit. A blood purification device is interposed between the arterial blood circuit and the venous blood circuit of the blood circuit. The blood purification device purifies the blood flowing in the blood circuit. A blood pump is arranged in the arterial blood circuit. The blood pump enables a liquid in the blood circuit to flow in a rotation direction. A control device performs a negative pressure applying process to release a negative pressure after applying the negative pressure to a flow route of an upstream side from an arrangement position of the blood pump in the arterial blood circuit.

The blood purification apparatus control device repeats application of the negative pressure and releases the negative pressure multiple times during the negative pressure applying process.

The blood purification apparatus further includes a substitution solution supplying line. The supplying line is connected to a section between the arrangement position of the blood pump in the arterial blood circuit and the distal end of the arterial blood circuit. The supplying line supplies the arterial blood circuit with a substitution solution to be substituted for blood inside the blood circuit. A switching device optionally switches between a closing state and a circulating state. In the closed state, it closes a flow route of the substitution solution supplying line. In the circulating state, it enables the substitution solution to be circulated. After treatment, the control device can perform the returning of blood by supplying the substitution solution to the blood circuit. This substitutes the blood inside the blood circuit with the substitution solution. During the returning of the blood, it can perform a venous returning blood process. Here, the returning of blood is performed by substituting the substitution solution for the blood from a connection portion connected to the substitution solution supplying line to a distal end of the venous blood circuit in the blood circuit. In an arterial returning blood process, the returning of the blood is performed by substituting the substitution solution for the blood from the connection portion connected to the substitution solution supplying line to a distal end of the arterial blood circuit in the blood circuit. The control device can perform a negative pressure applying process to release a negative pressure after applying the negative pressure to a flow route of an upstream side from an arrangement position of the blood pump in the arterial blood circuit. With the blood pump in a normal rotation direction during the returning blood process, this causes the switching device to switch over the substitution solution supplying line from the closing state to the circulating state.

The blood purification apparatus, the blood pump can be in a normal rotation and in a reverse rotation direction. The control device causes the blood pump to be in the normal rotation during the venous returning blood process. It causes the blood pump to be in the reverse rotation during the arterial returning blood process.

The blood purification apparatus further includes an arterial valve device. The arterial valve device is capable of opening and closing in the vicinity of the distal end of the arterial blood circuit. The valve can close and open a flow route. A venous valve device is capable of opening and closing in the vicinity of the distal end of the venous blood circuit. The valve can close and open a flow route. During the negative pressure applying process, the control device causes the arterial valve device to be in the closed state.

The blood purification apparatus control device alternately repeats the venous returning blood process and the arterial returning blood process multiple times. The negative pressure applying process is performed during the venous returning blood process.

The blood purification apparatus arterial returning blood process performs a pressure accumulation process. Here, the substitution solution is stored in a downstream side of the blood pump causing the blood pump to be in the normal rotation. The negative pressure applying process is performed during the pressure accumulation process.

The blood purification apparatus has an air trap chamber for removing air bubbles. The air trap is connected to the venous blood circuit or the arterial blood circuit on a downstream side from the blood pump.

The blood purification apparatus switching device includes an electromagnetic valve arranged in the substitution solution supplying line. The switching device can switch between the closing state and the circulating state. This occurs by switching the electromagnetic valve between a closed state and an opened state.

The blood purification apparatus switching device includes a peristaltic pump arranged in the substitution solution supplying line. The switching device can switch between the closing state and the circulating state by stopping or rotating the peristaltic pump.

The apparatus is provided with the control device. The control device can perform the negative pressure applying process. This releases the negative pressure after applying the negative pressure to the flow route of the upstream side from the arrangement position of the blood pump in the arterial blood circuit. Therefore, it is possible to suppress air bubbles from flowing to the distal end of the arterial blood circuit. Thus, it is possible to reduce the burden on health care workers.

The control device repeats the application of the negative pressure. This releases the negative pressure multiple times during the negative pressure applying process. This enables air bubbles to more reliably flow to the venous blood circuit side during the negative pressure applying process. Thus, it is possible to reliably suppress air bubbles from flowing to the distal end side of the arterial blood circuit. Also, it is possible to reduce the burden on the health care workers.

The control device, after treatment, performs the returning of blood by supplying the substitution solution to the blood circuit. This substitutes the blood inside the blood circuit with the substitution solution. During the returning of the blood, it can perform the venous returning blood process. Here, the returning of the blood is performed by substituting the substitution solution for the blood from the connection portion connected to the substitution solution supplying line to the distal end of the venous blood circuit in the blood circuit. The arterial returning blood process returning of the blood is performed by substituting the substitution solution for the blood from the connection portion connected to the substitution solution supplying line to the distal end of the arterial blood circuit in the blood circuit. The control device can perform the negative pressure applying process to release the negative pressure after applying the negative pressure to the flow route of the upstream side from an arrangement position of the blood pump in the arterial blood circuit. This enables the blood pump to be in the normal rotation during the returning blood process. The switching device switches over the substitution solution supplying line from the closing state to the circulating state. Thus, this enables air bubbles to flow to the venous blood circuit side during the negative pressure applying process. Also, it is possible to suppress air bubbles from flowing to the distal end side of the arterial blood circuit during the arterial returning blood process. Further, it is possible to reduce the burden on the health care workers.

The blood pump can be in the normal rotation and in the reverse rotation. The control device causes the blood pump to be in the normal rotation during the venous returning blood process. The control device causes the blood pump to be in the reverse rotation during the arterial returning blood process. Therefore, it is possible to excellently and reliably perform the returning of the blood by using the venous returning blood process and the arterial returning blood process.

The apparatus has the arterial valve device and is capable of opening and closing in the vicinity of the distal end of the arterial blood circuit. The valve can close and open the flow route. The venous valve device is capable of opening and closing in the vicinity of the distal end of the venous blood circuit. The valve can close and open the flow route. During the negative pressure applying process, the control device causes the arterial valve device to be in the closed state. Therefore, it is possible to reliably apply the negative pressure to the upstream side of the blood pump.

The control device alternately repeats the venous returning blood process and the arterial returning blood process multiple times. The negative pressure applying process is performed during the venous returning blood process. Therefore, during the returning blood process, it is possible to suppress coagulation of the blood from the connection portion, connected to the substitution solution supplying line, to the distal end of the venous blood circuit. Also, it suppresses coagulation of the blood circuit and the blood from the connection portion, connected to the substitution solution supplying line, to the distal end of the arterial blood circuit in the blood circuit. It is possible to suppress air bubbles from flowing to the distal end of the arterial blood circuit during the arterial returning blood process. Thus, it is possible to reduce the burden on the health care workers.

Before the arterial returning blood process, a pressure accumulation process is performed. Here, the substitution solution is stored in a downstream side of the blood pump by causing the blood pump to be in the normal rotation. The negative pressure applying process is performed during the pressure accumulation process. Therefore, it is possible to more reliably suppress air bubbles from flowing to the distal end of the arterial blood circuit during the arterial returning blood process.

The air trap chamber removing air bubbles is connected to the venous blood circuit or the arterial blood circuit of a downstream side from the blood pump. Therefore, during the negative pressure applying process, it is possible to reliably capture air bubbles by using the air trap chamber.

The switching device includes the electromagnetic valve arranged in the substitution solution supplying line. The switching device can switch between the closing state and the circulating state. This occurs by switching the electromagnetic valve between the closed state and the opened state. Therefore, it is possible to easily apply the apparatus to a device where supply of the physiological saline solution, as the substitution solution, is supplied to the blood circuit. This occurs using a self-weight after connecting the containing device, containing the physiological saline solution, to a base end of the substitution solution supplying line.

The switching device includes the peristaltic pump arranged in the substitution solution supplying line. The switching device can switch between the closing state and the circulating state by stopping or rotating the peristaltic pump. Therefore, it is possible to easily apply the apparatus to a device where supply of the dialysate as the substitution solution to the blood circuit is by rotating the peristaltic pump after connecting a base end of the substitution solution supplying line to a dialysate introduction line to supply dialysate to the blood purification device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a schematic view of a blood purification apparatus during a venous returning blood process according to an embodiment of the present disclosure.

FIG. 2 is a schematic view of the blood purification apparatus during a pressure accumulation process in an arterial returning blood process.

FIG. 3 is a schematic view of the blood purification apparatus during a returning blood process in the arterial returning blood process.

FIG. 4 is a schematic view of the blood purification apparatus during a negative pressure applying process.

FIG. 5 is a schematic view of the blood purification apparatus during the negative pressure applying process.

FIG. 6 is a flowchart of control details during the returning of blood in the blood purification apparatus when performing the negative pressure applying process during the venous returning blood process.

FIG. 7 is a flowchart illustrating control details during the returning of blood in the blood purification apparatus when performing the negative pressure applying process during the pressure accumulation process.

FIG. 8 is a schematic view of a blood purification apparatus according to another embodiment of the present disclosure.

FIG. 9 is a schematic view of a blood purification apparatus according to still another embodiment of the present disclosure.

FIG. 10 is a schematic view of the blood purification apparatus during the negative pressure applying process according to the embodiment.

DETAILED DESCRIPTION

Hereinafter, an embodiment of the present disclosure will be described in detail with reference to the drawings.

A blood purification apparatus includes a dialysis apparatus to perform dialysis treatment. As illustrated in FIG. 1, the blood purification apparatus is mainly configured to include a blood circuit with an arterial blood circuit 1 and a venous blood circuit 2. A dialyzer 3 (blood purification device) is interposed between the arterial blood circuit 1 and the venous blood circuit 2. The dialyzer 3 purifies blood flowing in the blood circuit. A blood pump 4, an arterial air trap chamber 5 and a venous air trap chamber 6 are arranged in the arterial blood circuit 1 and the venous blood circuit 2, respectively. A dialysis device B can supply dialysate to the dialyzer 3. A physiological saline solution supplying line 8 is a substitution solution supplying line. A containing device 9 contains a physiological saline solution as a substitution solution. An arterial air bubble detection device 10 and a venous air bubble detection device 11 are in the respective blood circuits 1, 2.

An arterial puncture needle is connected to a distal end of the arterial blood circuit 1. The peristaltic blood pump 4 and the arterial air trap chamber 5 are arranged in an intermediate portion of the arterial blood circuit 1. In contrast, a venous puncture needle is connected to a distal end of the venous blood circuit 2. The venous air trap chamber 6 is connected to an intermediate portion. The arterial air trap chamber 5 and the venous air trap chamber 6 have an air layer so as to be capable of capturing air bubbles. Also, they include a filtering net (not illustrated) to be capable of capturing a thrombus during returning of the blood, for example. The arterial air trap chamber 5 is arranged in a downstream side of the blood pump 4 in the arterial blood circuit 1 between the blood pump 4 and the dialyzer 3 in the arterial blood circuit 1.

The blood pump 4 includes a peristaltic pump arranged in the arterial blood circuit 1. The blood pump 4 can rotate in a normal rotation and in a reverse rotation. The blood pump can cause a liquid inside the blood circuit to flow in a rotation direction. That is, a peristaltically-actuated tube 1a, which has a softer material and a larger diameter than that of other flexible tubes configuring the arterial blood circuit 1, is connected to the arterial blood circuit 1. A roller is arranged in the blood pump 4. The roller peristaltically actuates the peristaltically-actuated tube 1a in a longitudinal direction. If the blood pump 4 is rotated in this way, the roller is rotated so as to peristaltically actuate the peristaltically-actuated tube 1a. This enables an internal liquid to flow in the rotation direction, rotation direction of the roller.

If the blood pump 4 is in the normal rotation, counter-clockwise rotation in the drawing, in a state where the arterial puncture needle and the venous puncture needle puncture a patient, blood of the patient passes through the arterial blood circuit 1 and reaches the dialyzer 3. The blood is purified by the dialyzer 3. The blood is subjected to air bubble removal in the venous air trap chamber 6. The blood passes through the venous blood circuit 2 and returns to an internal body of the patient. That is, the blood of the patient is extracorporeally circulated from the distal end of the arterial blood circuit 1 to the distal end of the venous blood circuit 2 in the blood circuit. The blood is purified by the dialyzer 3.

A housing unit of the dialyzer 3 has a blood introduction port 3a, a blood discharge port 3b, a dialysate introduction port 3c and a dialysate discharge port 3d. Among them, the arterial blood circuit 1 is connected to the blood introduction port 3a. The venous blood circuit 2 is connected to the blood discharge port 3b. In addition, the dialysate introduction port 3c and the dialysate discharge port 3d are respectively connected to a dialysate introduction line La and a dialysate discharge line Lb. The lines La, Lb extend from the dialysis device B.

The dialyzer 3 internally contains a plurality of hollow fibers. An interior of the hollow fibers is configured to be a flow route for the blood. A section between an outer peripheral surface of the hollow fibers and an inner peripheral surface of the housing unit is configured to be a flow route of the dialysate. The hollow fibers have multiple minute holes (pores) that penetrate the outer peripheral surface and the inner peripheral surface. This forms a hollow fiber membrane. In this configuration, impurities and the like within the blood can be transmitted into the dialysate via the membrane.

In contrast, in the dialysis device B, a duplex pump 17 is arranged across the dialysate introduction line La and the dialysate discharge line Lb. In a bypass line Lc, which bypasses the duplex pump 17, an ultrafiltration pump 18 is arranged to remove water from the patient's blood flowing within the dialyzer 3. Further, one end of the dialysate introduction line La is connected to the dialyzer 3 (dialysate introduction port 3c). The other end is connected to a dialysate supplying device (not illustrated). The device produces the dialysate with a predetermined concentration. In addition, one end of the dialysate discharge line Lb is connected to the dialyzer 3 (dialysate discharge port 3d). The other end is connected to a liquid discharge device (not illustrated). The dialysate supplied from the dialysate supplying device passes through the dialysate introduction line La and reaches the dialyzer 3. Thereafter, the dialysate passes through the dialysate discharge line Lb and is delivered to the liquid discharge device.

A pressure sensor 21 is connected to the venous air trap chamber 6 via a monitor tube. The sensor 21 can measure a liquid pressure (venous pressure) inside the venous air trap chamber 6. In addition, an overflow line 20 extends from an upper portion (air layer side) of the venous air trap chamber 6. An electromagnetic valve V4 is arranged in an intermediate portion of the overflow line 20. When the electromagnetic valve V4 is in an opened state, the liquid flowing within the blood circuit (priming solution and the like) can be overflowed via the overflow line 20.

The physiological saline solution supplying line 8 (substitution solution supplying line) has one end connected to a T-tube T. The T-tube is between an arrangement position of the blood pump 4 in the arterial blood circuit 1 and a distal end of the arterial blood circuit 1. A flow route (for example, a flexible tube or the like) can supply the arterial blood circuit 1 with the physiological saline solution (substitution solution) to be substituted for the blood inside the blood circuit. The containing device 9 contains a predetermined amount of the physiological saline solution. The device 9 is connected to the other end of the physiological saline solution supplying line 8. The air trap chamber 7 is connected to an intermediate portion. The reference numeral 16 in the drawing represents a tube detector consisting of a sensor for detecting presence or absence of the physiological saline solution supplying line 8.

In addition, an electromagnetic valve V3, as a switching device, is arranged in the physiological saline solution supplying line 8, according to the present embodiment. The electromagnetic valve V3 is disposed and is capable of opening and closing the physiological saline solution supplying line 8. The valve V3 can close and open the flow route. By switching the electromagnetic valve V3 between the closed state and the opened state, it is possible to optionally switch between a closing state and circulating state. The closing state and the valve V3 can close the flow route of the physiological saline solution supplying line 8. In the circulating state, the valve V3 can circulate the physiological saline solution (substitution solution). The electromagnetic valve V3 is configured so that particularly opening and closing operations are controlled by a control device 19 (to be described later).

Further, an electromagnetic valve V1, as an arterial valve device, and an electromagnetic valve V2, as a venous valve device, are arranged in the arterial and venous blood circuit lines 1 and 2, respectively. The valve V1 is arranged in the vicinity of the arterial puncture needle in the arterial blood circuit 1. This is a section between a connection portion, position of the T-tube T of the physiological saline solution supplying line 8, which is in the vicinity of the distal end of the arterial blood circuit 1 and the arterial puncture needle. The valve V2 is in the vicinity of the venous puncture needle in the venous blood circuit 2. This is a section between the venous air trap chamber 6, which is in the vicinity of the distal end of the venous blood circuit 2, and the venous puncture needle. The electromagnetic valves V1 and V2 can close and open the flow route in each arranged portion by performing opening and closing operations. In particular, they are configured so that the opening and closing operations during the returning of blood are controlled by the control device 19.

In addition, an arterial air bubble detection device 10 is arranged in the vicinity of the distal end of the arterial blood circuit 1 in the vicinity of the electromagnetic valve V1 as the arterial valve device. A venous air bubble detection device 11 is arranged in the vicinity of the distal end of the venous blood circuit 2 in the vicinity of the electromagnetic valve V2 as the venous valve device. The arterial air bubble detection device 10 and the venous air bubble detection device 11 include a sensor that can detect air bubbles in the liquid flowing inside the flow route. The devices 10, 11 are electrically connected to the control device 19. The reference numerals 12 and 13 and the reference numerals 14 and 15 represent a blood discriminator. This is a sensor or the like that discriminates whether or not the blood inside the flow route is circulated. A tube detector sensor or the like detects presence or absence of the arterial blood circuit 1 and the venous blood circuit 2. They are arranged in the vicinity of the distal end of the arterial blood circuit 1 and in the vicinity of the distal end of the venous blood circuit 2.

The dialysis device B according to the present embodiment internally includes the control device 19, with a microcontroller, for example. The control device 19 is electrically connected to actuators such as the blood pump 4 and the electromagnetic valve V3 (switching device), for example. Also, it is connected to sensors such as the arterial air bubble detection device 10, the venous air bubble detection device 11 and the blood discriminator 12 and 13. After the blood purification treatment, the control device can cause the electromagnetic valve V3 (switching device) to be in the circulating state. Here, the physiological saline solution (substitution solution) can be supplied to the blood circuit. Also, it can perform the returning of the blood by substituting the blood inside the blood circuit with the physiological saline solution (substitution solution).

More specifically, during the returning of the blood, the control device 19 can perform a venous returning blood process (refer to FIG. 1). The returning of the blood is performed by causing normal rotation of the blood pump 4 and substituting the physiological saline solution for the blood. The connection portion (position of the T-tube T) connected to the physiological saline solution supplying line 8 sends solution to the distal end of the venous blood circuit 2 in the blood circuit. An arterial returning blood process (refer to FIG. 3) returning of the blood is performed by reverse rotation of the blood pump 4 and substituting the physiological saline solution for the blood. The connection portion (position of the T-tube T) connected to the physiological saline solution supplying line 8 sends the solution to the distal end of the arterial blood circuit 1 in the blood circuit.

Here, as illustrated in FIGS. 4 and 5, the control device 19, according to the present embodiment, causes the blood pump 4 to be in the normal rotation and causes the electromagnetic valve V3 (switching device) to switch over, the physiological saline solution supplying line 8, from the closed state (closing state) to the opened state (circulating state). In this manner, the control device 19 applies a negative pressure to the flow route of the upstream side from the arrangement position of the blood pump 4 in the arterial blood circuit 1. Specifically, a section between the electromagnetic valve V1 (arterial opening/closing device) in the arterial blood circuit 1 and the peristaltically-actuated tube 1a, and a section between the connection portion (T-tube T) in the physiological saline solution supplying line 8 and the arrangement position of the electromagnetic valve V3 (switching device). Thereafter, the control device 19 performs a negative pressure applying process for releasing the negative pressure.

Even if air bubbles (air bubbles generated in the peristaltically-actuated tube 1a) are generated in the upstream side from the blood pump 4 during the blood purification treatment, the control device 19 performs the negative pressure applying process. This causes air bubbles generated by force of the released negative pressure to flow toward the venous blood circuit 2 side (downstream side from the blood pump 4). The air bubbles are captured by the arterial air trap chamber 5 or the venous air trap chamber 6. By performing the negative pressure applying process before the arterial returning blood process, it is possible to reliably avoid a case where air bubbles eventually flow into the patient side during the arterial returning blood process.

Next, FIG. 6 illustrates control details during the returning of the blood using the control device 19 according to the present embodiment. In this case, where the negative pressure applying process is performed during the venous returning blood process will be described.

If the returning of the blood starts after the blood purification treatment, the negative pressure applying process S1a is performed by the control of the control device 19. As illustrated in FIGS. 4 and 5, the negative pressure applying process S1a is performed causing the electromagnetic valve V1 (arterial valve device) to be in the closed state. Also, the control device 19 causes the electromagnetic valve V2 (venous valve device) to be in the opened state. The control device 19 causes the blood pump 4 to be in the normal rotation. The control device causes the electromagnetic valve V3 (switching device) to switch over from the closed state (refer to FIG. 4) to the opened state (refer to FIG. 5).

The switching control of the electromagnetic valve V3 (switching device) from the closed state to the opened state enables the physiological saline solution supplying line 8 to be switched over from the closing state to the circulating state. Therefore, it is possible to release the negative pressure after applying the negative pressure to the flow route of the upstream side from the arrangement position of the blood pump 4 in the arterial blood circuit 1. Specifically, the section between the electromagnetic valve V1 (arterial opening/closing device) in the arterial blood circuit 1 and the peristaltically-actuated tube 1a, and the section between the connection portion (T-tube T) in the physiological saline solution supplying line 8 and the arrangement position of the electromagnetic valve V3 (switching device)).

In this manner, by using the force of the released negative pressure, it is possible to cause air bubbles generated in the peristaltically-actuated tube 1a, for example, to flow to the downstream side. Thus, it is possible to capture air bubbles by the arterial air trap chamber 5 or the venous air trap chamber 6. In the present embodiment, in the negative pressure applying process S1a, the control device 19 controls the electromagnetic valve V3 (switching device). The valve V3 performs the opening and closing operations multiple times so that the physiological saline solution supplying line 8 is repeatedly switched over between the closing state and the circulating state multiple times. However, the electromagnetic valve V3 (switching device) may be switched over from the closed state to the opened state only once.

If the negative pressure applying process S1a is completed, the venous returning blood process S1 is performed. Thus, the returning of the blood is performed by substituting the physiological saline solution (substitution solution) for the blood. This occurs from the connection portion (position of the T-tube T) connected to the physiological saline solution supplying line 8 to the distal end of the venous blood circuit 2 in the blood circuit. As illustrated in FIG. 1, the venous returning blood process S1 is performed by causing the electromagnetic valve V1 (arterial valve device) to be in the closed state. The electromagnetic valve V2 (venous valve device) is in the opened state. The electromagnetic valve V3 (switching device) is in the opened state. The blood pump 4 moves in the normal rotation. The negative pressure applying process S1a is performed before the venous returning blood process S1, as described above. However, it may be performed in the middle of the venous returning blood process S1 or at the end of the venous returning blood process S1.

This first venous returning blood process S1 allows the returning of the blood to be performed by substituting the physiological saline solution (substitution solution) for a predetermined amount out of the blood. The amount is from the connection portion (position of the T-tube T) connected to the physiological saline solution supplying line 8 to the distal end of the venous blood circuit 2 in the blood circuit. Then, it is determined whether or not the physiological saline solution supplied by the first venous returning blood process S1 reaches a predetermined capacity (S2). If it is determined that the predetermined capacity is reached, the first venous returning blood process S1 is completed. The process proceeds to a pressure accumulation process S3. The predetermined amount in S2 can be understood by detecting the rotation time or the flow rate of the blood pump 4, for example.

The pressure accumulation process S3 is a process performed before the arterial returning blood process S4, and as illustrated in FIG. 2. It is performed by the electromagnetic valve V1 (arterial valve device) and the electromagnetic valve V2 (venous valve device) being in the closed state. The electromagnetic valve V3 (switching device) is in the opened state. The blood pump 4 moves in the normal rotation. The pressure accumulation process S3 enables the physiological saline solution (substitution solution) for use in the subsequent arterial returning blood process S4 to be stored inside the blood circuit of the downstream side from the arrangement portion of the blood pump 4.

If the pressure accumulation process S3 is completed, the arterial returning blood process S4 is performed. The arterial returning blood process S4 is a process where the returning of blood is performed by substituting the physiological saline solution (substitution solution) for the blood from the connection portion (position of the T-tube T) connected to the physiological saline solution supplying line 8 to the distal end of the arterial blood circuit 1 in the blood circuit. As illustrated in FIG. 3, the arterial returning blood process S4 is performed by the electromagnetic valve V1 (arterial valve device) being in the opened state. The electromagnetic valve V2 (venous valve device) is in the closed state. The electromagnetic valve V3 (switching device) is in the closed state. The blood pump 4 is moved in the reverse rotation.

This first arterial returning blood process S4 enables the returning of the blood to be performed by substituting the physiological saline solution (substitution solution) for the predetermined amount out of the blood. The amount is from the connection portion (position of the T-tube T) connected to the physiological saline solution supplying line 8 to the distal end of the venous blood circuit 2 in the blood circuit. Thereafter, it is determined whether or not the physiological saline solution supplied by the first arterial returning blood process S4 reaches a predetermined capacity (S5). If it is determined that the predetermined capacity is reached, the first arterial returning of the blood S4 is completed. The process proceeds to S6. The predetermined amount in S5 can be understood by detecting the rotation time or the flow rate of the blood pump 4, for example.

The process S6 is a process for determining whether or not the returning of blood amount for the blood circuit (arterial blood circuit 1 and the venous blood circuit 2) reaches the predetermined amount (that is, whether or not the predetermined amount of substitution solution is supplied). If it is determined not to reach the predetermined returning of blood amount, the process proceeds to S7. If it is determined whether or not the returning of blood amount for the venous blood circuit 2 reaches the predetermined amount (that is, whether or not the predetermined amount of substitution solution is supplied). Then, in S7, if the returning of blood amount for the venous blood circuit 2 is determined not to reach a predetermined value, the process returns to S1 so as to perform the venous returning blood process S1. In S7, if the returning of blood amount for the venous blood circuit 2 is determined that the predetermined value is reached, the process returns to S3 so as to perform the pressure accumulation process S3 and the arterial returning blood process S4.

In contrast, in S6, if the returning of blood amount for the arterial blood circuit 1 and the venous blood circuit 2 is determined that the predetermined value is reached, a series of control for the returning of blood is completed. That is, in the present embodiment, the control device 19 alternately performs the venous returning blood process S1 and the arterial returning blood process S4 multiple times. The entire blood in the blood circuit is set to be substituted with the physiological saline solution (substitution solution) by respectively performing the venous returning blood process S1 and the arterial returning blood process S4 over a predetermined number of times.

In the above-described case, the control device 19 alternately performs the venous returning blood process S1 and the arterial returning blood process S4 multiple times. Also, it performs the negative pressure applying process S1a during the venous returning blood process S1. Accordingly, during the returning blood process, it is possible to suppress the coagulation of the blood from the connection portion connected to the physiological saline solution supplying line 8 to the distal end of the venous blood circuit 2 in the blood circuit. Also, it suppresses coagulation of the blood from the connection portion connected to the physiological saline solution supplying line 8 to the distal end of the arterial blood circuit 1 in the blood circuit. During the arterial returning blood process S4, it is possible to suppress air bubbles from flowing to the distal end side of the arterial blood circuit 1. Therefore, it is possible to reduce the burden on the health care workers by avoiding a case where the arterial air bubble detection device 10 detects air bubbles and issues an alarm.

Next, with reference to FIG. 7, control details during the returning of blood using the control device 19, according to the present embodiment, will be described in a case where the negative pressure applying process is performed during the pressure accumulation process.

If the returning of the blood starts after the blood purification treatment, the venous returning blood process S1 is performed by the control of the control device 19. Here, the returning of the blood is performed by substituting the physiological saline solution (substitution solution) for the blood from the connection portion (position of the T-tube T) connected to the physiological saline solution supplying line 8 to the distal end of the venous blood circuit 2 in the blood circuit. As illustrated in FIG. 1, the venous returning blood process S1 is performed by causing the electromagnetic valve V1 (arterial valve device) to be in the closed state. The electromagnetic valve V2 (venous valve device) is in the opened state. The electromagnetic valve V3 (switching device) is to be in the opened state. The blood pump 4 is in the normal rotation.

This first venous returning blood process S1 allows the returning of the blood to be performed by substituting the physiological saline solution (substitution solution) for the predetermined amount out of the blood. The amount is from the connection portion (position of the T-tube T) connected to the physiological saline solution supplying line 8 to the distal end of the venous blood circuit 2 in the blood circuit. Then, it is determined whether or not the physiological saline solution supplied by the first venous returning blood process S1 reaches the predetermined capacity (S2). If it is determined that the predetermined capacity is reached, the first venous returning of blood S1 is completed. The process proceeds to the pressure accumulation process S3. The predetermined amount in S2 can be understood by detecting the rotation time or the flow rate of the blood pump 4, for example.

During the pressure accumulation process S3, the negative pressure applying process S3a is performed by the control of the control device 19. As illustrated in FIGS. 4 and 5, the negative pressure applying process S3a is performed by causing the electromagnetic valve V1 (arterial valve device) to be in the closed state. The electromagnetic valve V2 (venous valve device) is in the opened state. The blood pump 4 is in the normal rotation. The electromagnetic valve V3 is controlled (switching device) to switch over from the closed state (refer to FIG. 4) to the opened state (refer to FIG. 5).

The switching control of the electromagnetic valve V3 (switching device) from the closed state to the opened state enables the physiological saline solution supplying line 8 to be switched over from the closing state to the circulating state. Therefore, it is possible to release the negative pressure after applying the negative pressure to the flow route of the upstream side from the arrangement position of the blood pump 4 in the arterial blood circuit 1, specifically, the section between the electromagnetic valve V1 (arterial opening/closing device) in the arterial blood circuit 1 and the peristaltically-actuated tube 1a. Also, the section between the connection portion (T-tube T) in the physiological saline solution supplying line 8 and the arrangement position of the electromagnetic valve V3 (switching device).

In this manner, by using the force of the released negative pressure, it is possible for the air bubbles generated in the peristaltically-actuated tube 1a, for example, to flow to the downstream side. Thus, it is possible to capture the air bubbles by the arterial air trap chamber 5 or the venous air trap chamber 6. In the present embodiment, in the negative pressure applying process S3a, the control device 19 controls the electromagnetic valve V3 (switching device) to perform the opening and closing operations multiple times. Thus, the physiological saline solution supplying line 8 is repeatedly switched over between the closing state and the circulating state, multiple times. However, the electromagnetic valve V3 (switching device) may be switched over from the closed state to the opened state only once.

If the negative pressure applying process S3a is completed, as illustrated in FIG. 2, the electromagnetic valve V1 (arterial valve device) and the electromagnetic valve V2 (venous valve device) are caused to be in the closed state. The electromagnetic valve V3 (switching device) is caused to be in the opened state. The blood pump 4 is caused to be in the normal rotation to perform the press accumulation process S3. The pressure accumulation process S3 enables the physiological saline solution (substitution solution) for use in the subsequent arterial returning blood process S4 to be stored inside the blood circuit of the downstream side from the arrangement portion of the blood pump 4.

If the pressure accumulation process S3 is completed, the arterial returning blood process S4 is performed. The arterial returning blood process S4 is a process where the returning of the blood is performed by substituting the physiological saline solution (substitution solution) for the blood. This occurs from the connection portion (position of the T-tube T) connected to the physiological saline solution supplying line 8 to the distal end of the arterial blood circuit 1 in the blood circuit. As illustrated in FIG. 3, the arterial returning blood process S4 is performed by causing the electromagnetic valve V1 (arterial valve device) to be in the opened state. The electromagnetic valve V2 (venous valve device) is in the closed state. The electromagnetic valve V3 (switching device) is in the closed state. The blood pump 4 is in the reverse rotation direction.

This first arterial returning blood process S4 enables the returning of blood to be performed by substituting the physiological saline solution (substitution solution) for the predetermined amount out of the blood. This amount is from the connection portion (position of the T-tube T) connected to the physiological saline solution supplying line 8 to the distal end of the venous blood circuit 2 in the blood circuit. Thereafter, it is determined whether or not the physiological saline solution supplied by the first arterial returning blood process S4 reaches the predetermined capacity (S5). If it is determined that the predetermined capacity is reached, the first arterial returning blood process S4 is completed. The process proceeds to S6. The predetermined amount in S5 can be understood by detecting the rotation time or the flow rate of the blood pump 4, for example.

The process S6 is a process to determine whether or not the venous returning blood process S1 and the arterial returning blood process S4 are performed over the predetermined number of times. If it is determined not to be performed over the predetermined number of times, similar to the control in FIG. 6, the control device 19 controls the venous returning blood process S1 or the pressure accumulation process S3 to be performed again based on the determination in S7. If it is determined to be performed over the predetermined number of times, a series of control for the returning of the blood is completed. That is, in the present embodiment, the control device 19 alternately performs the venous returning blood process S1 and the arterial returning blood process S4 multiple times. The entire amount of blood in the blood circuit is set to be substituted with the physiological saline solution (substitution solution) by respectively performing the venous returning blood process S1 and the arterial returning blood process S4 over the predetermined number of times.

In the above-described case, before the arterial returning blood process S4, the pressure accumulation process S3 is performed where the physiological saline solution (substitution solution) is stored in the downstream side of the blood pump 4. Here, the blood pump 4 is in the normal rotation. The negative pressure applying process S3a is performed during the pressure accumulation process S3. Accordingly, it is possible to reliably suppress air bubbles from flowing to the distal end side of the arterial blood circuit 1 during the arterial returning blood process S4. That is, the negative pressure applying process S3a is performed during the pressure accumulation process S3 immediately before the arterial returning blood process S4. In this manner, it is possible to reliably suppress air bubbles from flowing to the distal end side of the arterial blood circuit 1 during the arterial returning blood process S4.

In addition, similar to the control in FIG. 6, the control device 19 alternately performs the venous returning blood process S1 and the arterial returning blood process S4 multiple times. Also, it performs the negative pressure applying process S3a during the pressure accumulation process S3. Accordingly, during the returning of the blood, it is possible to suppress the coagulation of the blood from the connection portion connected to the physiological saline solution supplying line 8 to the distal end of the venous blood circuit 2 in the blood circuit. Also, it is possible to suppress the coagulation of the blood from the connection portion connected to the physiological saline solution supplying line 8 to the distal end of the arterial blood circuit 1 in the blood circuit. During the arterial returning blood process S4, it is possible to suppress air bubbles from flowing to the distal end side of the arterial blood circuit 1. Therefore, it is possible to reduce the burden on the health care workers by avoiding a case where the arterial air bubble detection device 10 detects air bubbles and issues the alarm.

According to the present embodiment, the apparatus is provided with the control device 19 that can perform the negative pressure applying processes (S1a and S3a) to release the negative pressure after applying the negative pressure to the flow route of the upstream side from the arrangement position of the blood pump 4 in the arterial blood circuit 1. Therefore, it is possible to suppress air bubbles from flowing to the distal end side of the arterial blood circuit 1. Also, it is possible to reduce the burden on the health care workers. The negative pressure applying process, without being limited to the time of the returning of the blood, may be performed during the treatment or during the priming. The negative pressure applying process is advantageous if the negative pressure is released after applying the negative pressure to the flow route of the upstream side from the arrangement position of the blood pump 4 in the arterial blood circuit 1.

That is, by applying the negative pressure to the flow route of the upstream side from the arrangement position of the blood pump 4 in the arterial blood circuit 1, it is possible to increase a volume of air bubbles, thereby increasing buoyance. Accordingly, it is possible to allow air bubbles to easily flow by subsequently releasing the negative pressure. In addition, after applying the negative pressure, it is possible to change the flow speed of the liquid inside the flow route by releasing the negative pressure. Therefore, it is possible to eliminate stagnation of air bubbles inside the blood circuit. When the blood circuit is not filled with the blood during the treatment, or even when the blood circuit is not filled with the priming solution during the priming, it is possible to easily remove air bubbles by performing the negative pressure applying process.

In particular, in the present embodiment, during the process of the returning of the blood, the blood pump 4 moves in the normal rotation and the electromagnetic valve V3 (switching device) is switched over on the physiological saline solution supplying line 8 (substitution solution supplying line) from the closed state to the opened state (from the closing state to the circulating state). In this manner, it is possible to perform the negative pressure applying processes (S1a and S3a) to release the negative pressure after applying the negative pressure to the flow route of the upstream side from the arrangement position of the blood pump 4 in the arterial blood circuit 1. Therefore, by allowing air bubbles to flow to the venous blood circuit 2 during the negative pressure applying processes (S1a and S3a), it is possible to suppress air bubbles from flowing to the distal end side of the arterial blood circuit 1 during the arterial returning blood process S4. Thus, it is possible to reduce the burden on the health care workers.

In addition, during the negative pressure applying processes (S1a and S3a), the negative pressure is repeatedly applied. The negative pressure is repeatedly released multiple times by the control device 19. This repeatedly causes the electromagnetic valve V3 (switching device) to switch over between the closing state and the circulating state. Accordingly, by allowing air bubbles to reliably flow to the venous blood circuit 2 during the negative pressure applying processes (S1a and S3a), it is possible to reliably suppress air bubbles from flowing to the distal end side of the arterial blood circuit 1 during the arterial returning blood process S4. Thus, it is possible to reduce the burden on the health care workers.

Further, the blood pump 4 can be in the normal rotation and in the reverse rotation. The control device 19 causes the blood pump 4 to be in the normal rotation during the venous returning blood process S1. It causes the blood pump 4 to be in the reverse rotation during the arterial returning blood process S4. Accordingly, it is possible to excellently and reliably perform the returning of blood by using the venous returning blood process S1 and the arterial returning blood process S4. In addition, the apparatus is provided with the electromagnetic valve V1 (arterial valve device) that can close and open the flow route. The valve V1 is disposed in the vicinity of the distal end of the arterial blood circuit 1. The valve V1 openable and closeable with respect to the flow route. The electromagnetic valve V2 (venous valve device) can close and open the flow route. The valve V2 is disposed in the vicinity of the distal end of the venous blood circuit 2. The valve V2 is openable and closeable. The control device 19 causes the electromagnetic valve V1 (arterial valve device) to be in the closed state in the negative pressure applying processes (S1a and S3a). Therefore, it is possible to reliably apply the negative pressure to the upstream side of the blood pump 4.

The air trap chambers remove air bubbles in the present embodiment. The arterial air trap chamber 5 and the venous air trap chamber 6 are connected to the venous blood circuit 2 and the arterial blood circuit 1 of the downstream side (dialyzer 3 side) from the blood pump 4. Therefore, in the venous returning blood process S1, it is possible to reliably capture air bubbles by using the air trap chambers (the arterial air trap chamber 5 and the venous air trap chamber 6). Either the arterial air trap chamber 5 or the venous air trap chamber 6 may be connected to the blood circuit.

In the present embodiment, the switching device is optionally switched between the closing state and circulating state. In the closing state, it closes the flow route of the physiological saline solution supplying line 8 (substitution solution supplying line). In the circulating state, it enables the physiological saline solution (substitution solution) to be circulated. The electromagnetic valve V3 is arranged in the physiological saline solution supplying line 8. The closing state and the circulating state can be switched over to each other by switching the electromagnetic valve V3 between the closed state and the opened state. Therefore, it is possible to easily apply the present embodiment to a case where the physiological saline solution, as the substitution solution, is supplied to the blood circuit, using the self-weight, by connecting the containing device 9, containing the physiological saline solution, to the base end of the physiological saline solution supplying line 8.

The switching device according to the present embodiment is configured to have the electromagnetic valve V3 arranged in the physiological saline solution supplying line 8. However, instead of this configuration, a configuration as illustrated in FIG. 8 may be employed. As illustrated in FIG. 8, instead of the physiological saline solution supplying line 8, a substitution line 22 (substitution solution supplying line) may be employed. Its distal end is connected to the T-tube T and its base end is connected to the dialysate introduction line La, inside the dialysis device B. The peristaltic pump 23 (switching device) may be arranged in the intermediate portion of the substitution line 22.

In this case, the switching device which can optionally switch between the closing state and circulating state. In the closing state, it closes the flow route of the substitution line 22 (substitution solution supplying line). In the circulating state, it enables the physiological saline solution (substitution solution) to be circulated. The peristaltic pump 23 is arranged in the substitution line 22 (substitution solution supplying line). The closing state and the circulating state can be switched over to each other by stopping or rotating the peristaltic pump 23. Therefore, it is possible to easily apply the present embodiment to a case where the physiological saline solution, as the substitution solution, is supplied to the blood circuit by connecting the base end of the substitution solution supplying line 22 to the dialysate introduction line La. The introduction line supplies the dialysate to the dialyzer 3 (blood purification device) and by rotating the peristaltic pump 23 (dialysate infusing pump or the like).

Further, as illustrated in FIG. 9, this configuration can also be applied to apparatus that do not include the substitution solution supplying line (physiological saline solution supplying line 8) and the switching device (electromagnetic valve V3 or peristaltic pump 23) as in the above-described embodiment. In this case, when the retransfusion is performed, as illustrated in FIG. 9, the electromagnetic valves V1 and V2 are in the opened state. An electromagnetic valve V6 of the dialysate introduction line La is in the opened state. An electromagnetic valve V5 of the dialysate discharge line Lb is in the closed state. The duplex pump 17 is rotated. The blood pump 4 is in the reverse rotation. In this manner, by means of back-filtration of the dialysate from the dialysate introduction line La to the blood circuit side, it is possible to substitute the blood for the dialysate (substitution solution) subjected to the back-filtration.

During the returning of the blood, it is preferable to set the rotation amount (flow rate) of the blood pump 4 to be approximately half the rotation amount (flow rate) of the duplex pump 17. This allows the dialysate as the substitution solution subjected to the back-filtration to flow to both of the arterial blood circuit 1 and the venous blood circuit 2. This enables the arterial returning blood process and the venous returning blood process to be performed simultaneously. The venous returning blood process may be separately performed after stopping the blood pump 4, by setting the rotation amount (flow rate) of the blood pump 4 to be approximately equal to the rotation amount (flow rate) of the duplex pump 17 so as to perform the arterial returning blood process.

In the returning of the blood by means of the back-filtration as described above, the negative pressure applying process is performed in the following manner. As illustrated in FIG. 10, during the blood purification treatment (hemodialysis treatment), the electromagnetic valve V1 (arterial valve device) is in the closed state. The blood pump 4 is in the normal rotation. Thus, it is possible to apply the negative pressure to the flow route of the upstream side from the arrangement position of the blood pump 4 in the arterial blood circuit 1, flow route between the electromagnetic valve V1 and the arrangement position of the blood pump 4. In this manner, it is possible to increase the volume and the buoyance of air bubbles which are present in the flow route of the upstream side from the arrangement position of the blood pump 4 in the arterial blood circuit 1, flow route between the electromagnetic valve V1 and the arrangement position of the blood pump 4. Accordingly, it is possible to allow air bubbles to easily flow by subsequently causing the electromagnetic valve V1 (arterial valve device) to be in the opened state and releasing the negative pressure, for example. Thus, it is possible to easily remove air bubbles. In this case, the electromagnetic valve V1 functions as a negative pressure applying device.

Hitherto, the present embodiments have been described, but the present disclosure is not limited thereto. The pressure accumulation process S3 may not be necessary if a rotation source such as a peristaltic pump is arranged in the intermediate portion of the substitution solution supplying line, for example. In addition, in the present embodiments, during the arterial returning blood process S4, the blood pump 4 is caused to be in the reverse rotation. However, instead of this configuration, the rotation source such as the peristaltic pump may be arranged in the intermediate portion of the substitution solution supplying line, for example, and the peristaltic pump may be allowed to perform an operation that is the same as the above-described operation. Alternatively, a configuration may be employed where a potential energy generated based on an installation height of the containing device 9 is used to supply the physiological saline solution (substitution solution) inside the containing device 9 into the blood circuit. The present embodiments are employed in the dialysis apparatus used during the dialysis treatment. However, the present embodiments may be employed in other apparatuses that can extracorporeally circulate and purify the blood of the patient (for example, blood purification apparatuses, plasma adsorption apparatuses and the like which are used in a blood filtering dialysis method, a blood filtering method and AFBF).

If there is provided a blood purification apparatus including a control device which can perform a negative pressure applying process to release a negative pressure after applying the negative pressure to a flow route of an upstream side from an arrangement position of a blood pump in an arterial blood circuit, the present disclosure can also be employed in those with other additional functions.

The present disclosure has been described with reference to the preferred embodiments and modifications. Obviously, other modifications and alternations will occur to those of ordinary skill in the art upon reading and understanding the preceding detailed description. It is intended that the present disclosure be construed to include all such alternations and modifications insofar as they come within the scope of their appended claims or equivalents.

What is claimed is:

1. A blood purification apparatus comprising:
a blood circuit with an arterial blood circuit and a venous blood circuit to extracorporeally circulate blood of a patient from a distal end of the arterial blood circuit to a distal end of the venous blood circuit;
a blood purification device is interposed between the arterial blood circuit and the venous blood circuit of the blood circuit, the blood purification device purifies the blood flowing in the blood circuit;
a blood pump is arranged in the arterial blood circuit and enables a liquid in the blood circuit to flow in a rotation direction, at least one valve is arranged in the arterial blood circuit, a switching device is arranged in a substitute solution supplying line, the switching device is connected to the blood circuit via the substitution solution supply line; and
a controller programmed to generate a negative pressure in the blood circuit by:
(a) manipulating the rotational direction of the blood pump in a first direction;
(b) closing the at least one valve in the arterial blood circuit and closing the switching device in the substitute solution supplying line while the pump rotates in the first direction to generate a negative pressure in the blood circuit;
(c) creating the negative pressure in the blood circuit;
the controller further programmed to release the negative pressure in the blood circuit by:
(a) reversing direction of the blood pump;
(b) opening the switching device; and
(c) enabling blood from the arterial blood circuit to be drawn into the venous blood circuit while terminating withdrawal of blood from a patient.

2. The blood purification apparatus according to claim 1, wherein the controller repeats application of the negative pressure and release of the negative pressure multiple times during the negative pressure applying process.

3. The blood purification apparatus according to claim 1, further comprising:
a substitution solution supplying line connected to a section between the arrangement position of the blood pump in the arterial blood circuit and the distal end of the arterial blood circuit, the substitution solution supplying line supplying the arterial blood circuit with a substitution solution to be substituted for blood inside the blood circuit; and
the switching device optionally switching between a closing state, for closing a flow route of the substitution solution supplying line, and a circulating state for enabling the substitution solution to be circulated,
wherein after treatment, the controller performs returning of the blood by supplying the substitution solution to the blood circuit and substituting the blood inside the blood circuit with the substitution solution, and during the returning of the blood, the controller performs a venous returning blood process, where the returning of blood is performed by substituting the substitution solution for the blood from a connection portion connected to the substitution solution supplying line to the distal end of the venous blood circuit, also in performing an arterial returning blood process, where the returning of blood is performed by substituting the substitution solution for the blood from the connection portion connected to the substitution solution supplying line to the distal end of the arterial blood circuit in the blood circuit, the controller performs a negative pressure applying process to release a negative pressure after applying the negative pressure to the flow route of the upstream side from the arrangement position of the blood pump in the arterial blood circuit, by allowing the blood pump to be in a normal rotation during the returning blood process and causing the switching device to switch over the substitution solution supplying line from the closing state to the circulating state.

4. The blood purification apparatus according to claim 3, wherein the blood pump can be in a normal rotation and in a reverse rotation; and
wherein the controller causes the blood pump to be in the normal rotation during the venous returning blood process, and causes the blood pump to be in the reverse rotation during the arterial returning blood process.

5. The blood purification apparatus according to claim 1, further comprising:
an arterial valve device, capable of opening and closing, disposed in the vicinity of the distal end of the arterial blood circuit, the arterial valve device can close and open a flow route; and
a venous valve device, capable of opening and closing, disposed in the vicinity of the distal end of the venous blood circuit, the venous valve device can close and open a flow route,
wherein during the negative pressure applying process, the controller causes the arterial valve device to be in the closed state.

6. The blood purification apparatus according to claim 3, wherein the controller alternately repeats the venous returning blood process and the arterial returning blood process multiple times; and
the negative pressure applying process is performed during the venous returning blood process.

7. The blood purification apparatus according to claim 3, wherein before the arterial returning blood process, a pressure accumulation process is performed where the substitution solution is stored in a downstream side of the blood pump by causing the blood pump to be in the normal rotation, and
wherein the negative pressure applying process is performed during the pressure accumulation process.

8. The blood purification apparatus according to claim 1, wherein an air trap chamber, for removing air bubbles, is connected to the venous blood circuit or the arterial blood circuit on a downstream side from the blood pump.

9. The blood purification apparatus according to claim 3, wherein the switching device includes an electromagnetic valve arranged in the substitution solution supplying line, and wherein the switching device can switch between the closing state and the circulating state by switching over the electromagnetic valve between a closed state and an opened state.

10. The blood purification apparatus according to claim 3, wherein the switching device includes a peristaltic pump arranged in the substitution solution supplying line, and wherein the switching device can switch between the closing state and the circulating state by stopping or rotating the peristaltic pump.

* * * * *